(12) United States Patent
Zitnick et al.

(10) Patent No.: US 11,045,219 B2
(45) Date of Patent: Jun. 29, 2021

(54) METHOD FOR PROVIDING ACCESS FOR A SURGICAL PROCEDURE

(71) Applicant: Titan Medical Inc., Toronto (CA)

(72) Inventors: David Allen Zitnick, Providence, RI (US); Leonard Faria, Swansea, MA (US); Dustin Gaidos, Milton, MA (US)

(73) Assignee: TITAN MEDICAL INC., Toronto (CA)

( * ) Notice: Subject to any disclaimer, the term of this patent is extended or adjusted under 35 U.S.C. 154(b) by 135 days.

(21) Appl. No.: 16/531,534

(22) Filed: Aug. 5, 2019

(65) Prior Publication Data

US 2019/0350621 A1 Nov. 21, 2019

Related U.S. Application Data

(63) Continuation of application No. 15/552,993, filed as application No. PCT/CA2016/000054 on Feb. 26, 2016, now Pat. No. 10,368,909.

(Continued)

(51) Int. Cl.
*A61B 17/34* (2006.01)
*A61B 46/10* (2016.01)
*A61B 90/40* (2016.01)

(52) U.S. Cl.
CPC ...... *A61B 17/3423* (2013.01); *A61B 17/3417* (2013.01); *A61B 17/3421* (2013.01);
(Continued)

(58) Field of Classification Search
CPC ............ A61B 17/3423; A61B 17/3431; A61B 17/3498; A61B 17/3417; A61B 17/3462;
(Continued)

(56) References Cited

U.S. PATENT DOCUMENTS 5,972,020 A 10/1999 Carpentier et al.
6,024,736 A * 2/2000 de la Torre ........ A61B 17/3423
128/898

(Continued)

FOREIGN PATENT DOCUMENTS

CA 2 680 915 A1 3/2010
CA 2 701 866 A1 10/2010
(Continued)

OTHER PUBLICATIONS

Alexis, Wound Protectors/Retractors, Applied Medical, www.appliedmedical.com/alexis (2016) in 6 pages.
(Continued)

*Primary Examiner* — Pedro Philogene
(74) *Attorney, Agent, or Firm* — Knobbe, Martens, Olson & Bear, LLP (57) ABSTRACT

An apparatus and method for providing surgical access to a body cavity of a living animal through an access port inserted in a wall of the body cavity is disclosed. The apparatus includes a collapsible volume having an opening for sealingly receiving a surgical apparatus. The apparatus also includes an access coupler disposed at a distal end of the collapsible volume, the access coupler being operably configured to sealingly couple to an opening in the access port placing the collapsible volume in fluid communication with the body cavity. The collapsible volume is operably configured to collapse to permit the surgical apparatus to be inserted through the access coupler into the body cavity.

20 Claims, 6 Drawing Sheets

Related U.S. Application Data (60) Provisional application No. 62/121,357, filed on Feb. 26, 2015.

(52) U.S. Cl.
CPC .......... *A61B 17/3462* (2013.01); *A61B 46/10* (2016.02); *A61B 90/40* (2016.02); *A61B 2017/3492* (2013.01)

(58) Field of Classification Search
CPC ..... A61B 17/3492; A61B 46/10; A61B 90/40; A61B 2017/3492
USPC .................................................. 600/184–219
See application file for complete search history.

(56) References Cited

U.S. PATENT DOCUMENTS

| | | | | |
|---|---|---|---|---|
| 8,425,410 | B2* | 4/2013 | Murray | A61B 17/3462 600/203 |
| 8,485,970 | B2* | 7/2013 | Widenhouse | A61B 1/018 600/201 |
| 2008/0033344 | A1 | 2/2008 | Mantell | |
| 2010/0312061 | A1* | 12/2010 | Hess | A61B 17/3423 600/201 |
| 2014/0235949 | A1 | 8/2014 | Smith | |
| 2018/0049770 | A1 | 2/2018 | Zitnick et al. | |
| 2019/0059935 | A1 | 2/2019 | Faria et al. | |

FOREIGN PATENT DOCUMENTS

| | | |
|---|---|---|
| WO | WO 2005/013832 A1 | 2/2005 |
| WO | WO 2016/134452 | 9/2016 |

OTHER PUBLICATIONS

GelPOINT, Advanced Access Platforms, Applied Medical, www.appliedmedical.com/gelpoint (2017) in 6 pages.
GelPort, Laparoscopic System, Applied Medical, www.appliedmedical.com/gelport (2015) in 2 pages.
International Search Report & Written Opinion mailed by Canadian Intellectual Property Office dated May 4, 2016 in the corresponding PCT application No. PCT/CA2016/000054.
SurgiSleeve Wound Protector with Retraction Ring, COVIDIEN (2015) in 3 pages.

* cited by examiner

METHOD FOR PROVIDING ACCESS FOR A SURGICAL PROCEDURE

CROSS-REFERENCE TO RELATED APPLICATION

This application is a continuation of U.S. application Ser. No. 15/552,993, filed on Aug. 23, 2017 and issued as U.S. Pat. No. 10,368,909 on Aug. 6, 2019, which is a U.S. national phase application under 35 U.S.C. § 371 of International Application No. PCT/CA2016/000054, filed on Feb. 26, 2016 and published as WO 2016/134452 A1 on Sep. 1, 2016, which is based on and claims the benefit of priority from U.S. Provisional Application No. 62/121,357, filed Feb. 26, 2015. The entire disclosures of all of the above applications are incorporated herein by reference.

BACKGROUND

1. Field

This disclosure relates to apparatus used for surgical procedures and more particularly to providing access to a body cavity of a living animal for robotic and/or laparoscopic surgical instruments and equipment during the surgical procedure.

2. Description of Related Art

In robotic and laparoscopic surgery it is common to provide access to a body cavity of a patient through an access device. An incision is made by a surgeon in a wall of the body cavity and the access device is inserted into the incision to provide a sealed entry point for a surgical device such as a laparoscopic instrument. For robotic and laparoscopic surgery, the access device may be required to provide a seal to any instrument inserted into the body cavity through the access device. The seal maintains insufflation pressure in the body cavity during insertion and subsequent movement of the instrument. The access device further facilitates insufflation of the body cavity and the removal of smoke produced during electrocauterization of tissues within the body cavity, while maintaining the seal. Commonly available access devices include surgical trocars such as those manufactured by Covidien PLC of Dublin, Ireland or by Stryker Corporation of Michigan, USA. Other types of access devices include wound protector/retractors such as the Alexis wound protector manufactured by Applied Medical Resources Corporation of Rancho Santa Margarita, Calif. and the SurgiSleeve™ wound protector manufactured by Covidien PLC. Wound retractors generally provide open access to the body cavity and are often used in conjunction with cap that covers the wound protector and provides a seal and a point of entry to the body cavity. Examples of available caps/sleeves that work with wound protectors are the GelPort laparoscopic system and the GelPOINT access platform, both manufactured by Applied Medical of California, USA.

SUMMARY

In accordance with one disclosed aspect there is provided an apparatus for providing surgical access to a body cavity of a living animal through an access port inserted in a wall of the body cavity. The apparatus includes a collapsible volume having an opening for sealingly receiving a surgical apparatus. The apparatus also includes an access coupler disposed at a distal end of the collapsible volume, the access coupler being operably configured to sealingly couple to an opening in the access port to place the collapsible volume in fluid communication with the body cavity. The collapsible volume is operably configured to collapse to permit the surgical apparatus to be inserted through the access coupler into the body cavity.

The access port may include an inlet for receiving a fluid flow for insufflating the body cavity and the collapsible volume may be subjected to an insufflation pressure in the body cavity.

The access coupler may be operably configured to initiate fluid communication between the body cavity and the collapsible volume when coupled to the opening in the access port.

The access port may include an access valve disposed to close the opening in the access port prior to the access coupler sealingly coupling to the opening.

The access valve may include a sealing element operably configured to be displaced by the access coupler when the access coupler is coupled to the opening in the access port.

The access port may include an outlet for expelling fluid from the body cavity.

The access coupler may include a barbed end operable to engage corresponding features within the opening in the access port for retaining the access coupler within the opening.

The collapsible volume may include a flexible sleeve.

The flexible sleeve may include a transparent portion operable to permit at least a portion of the surgical apparatus to be viewed while being inserted through the access coupler and the opening in the access port.

At least a portion of the collapsible volume may include a bellowed conduit.

The opening for sealingly receiving the surgical apparatus may include a collar for sealing to the surgical apparatus.

The collar may have a non-circular cross section for receiving and sealing to a surgical apparatus having a corresponding non-circular cross section.

The surgical apparatus received in the opening of the collapsible volume may include at least one of a camera for viewing an interior of the body cavity, an illumination source for illuminating the interior of the body cavity, a wash tube for delivering a wash fluid for cleaning a lens associated with one of the camera and the illumination source, and a bore for receiving a laparoscopic surgery instrument.

The compressible volume may be further operably configured to permit lateral movement of the surgical apparatus with respect to the access coupler to facilitate alignment of the surgical instrument for insertion through the access port.

The collapsible volume may be sized to accommodate at least one line extending through the collapsible volume and the access port into the body cavity.

The at least one line may include one of an electrical signal line, an optical signal line, a power line, and a wash tube for cleaning a lens associated with a camera disposed on a distal end of the surgical apparatus.

In accordance with another disclosed aspect there is provided a method for providing surgical access to a body cavity of a living animal through an access port inserted in a wall of the body cavity. The method involves sealingly receiving a surgical apparatus through an opening in a collapsible volume, and sealingly coupling an access coupler disposed at a distal end of the collapsible volume to an opening in the access port to place the collapsible volume in fluid communication with the body cavity. The method also involves causing the collapsible volume to collapse to permit the surgical apparatus to be inserted through the access coupler into the body cavity.

Other aspects and features of the present disclosure will become apparent to those ordinarily skilled in the art upon review of the following description of specific embodiments of the disclosure in conjunction with the accompanying figures.

BRIEF DESCRIPTION OF THE DRAWINGS

In drawings which illustrate embodiments of the invention.

DETAILED DESCRIPTION

Figure 1:
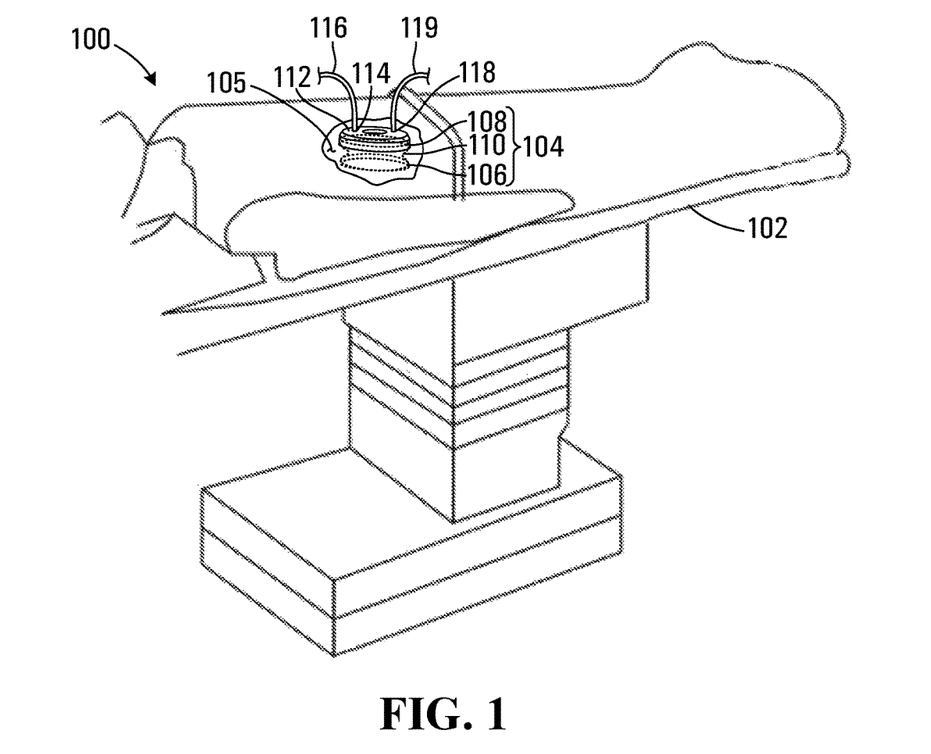
FIG. 1 is a depiction of a human patient undergoing a surgical procedure.

Referring to FIG. 1, a human patient 100 is shown on a surgical table 102. The patient 100 has had an access device 104 inserted in the abdominal wall 105 to permit access to the patient's abdominal body cavity for a surgical procedure. In this embodiment the access device 104 (shown in hidden detail in FIG. 1) is a wound protector/retractor having a resilient internal ring 106 and a flexible or rigid external ring 108 joined by a sleeve 110. To insert the wound retractor, a surgeon makes an incision in abdominal wall 105 and deforms the internal ring 106 to facilitate insertion through the incision. The internal ring 106 then retracts inside the body cavity and the internal and external ring 108 on either side of the incision hold the access device 104 in place within the abdominal wall 105.

In the embodiment shown, an access port 112 is configured to sealingly engage the external ring 108 of the access device 104 providing a sealed point of entry into the body cavity. The access port 112 includes an inlet 114 for receiving a fluid flow from an insufflation line 116. Insufflation of the abdominal body cavity with a gas such as carbon dioxide distends the abdomen providing for entry and sufficient operating space for manipulation of surgical instruments during the surgical procedure. In this embodiment access port 112 also includes an outlet 118 in communication with an evacuation line 119 for expelling fluid from the body cavity. The expelled fluid may include smoke and other vapors produced by electrocauterization of tissue, for example. The inlet and outlet ports 114 and 118 may be implemented using standard fluid connections such as Luer taper connections.

In an alternative embodiment the access port 112 may be implemented using a surgical trocar (not shown). Surgical trocars generally include a cannula that is either inserted directly through the incision or inserted through a capped access device such as a wound retractor. The cannula has a bore that permits insertion of instruments into the body cavity and may also include an insufflation inlet and an evacuation outlet. Whether received directly in the incision or through an access device 104, the trocar provides a sealed point of entry to the body cavity, as in the case of the access port 112 shown in FIG. 1.

In other embodiments surgery may be performed in body cavities other than an abdominal body cavity of the patient 100 or the surgery may be performed on an animal.

Figure 2:
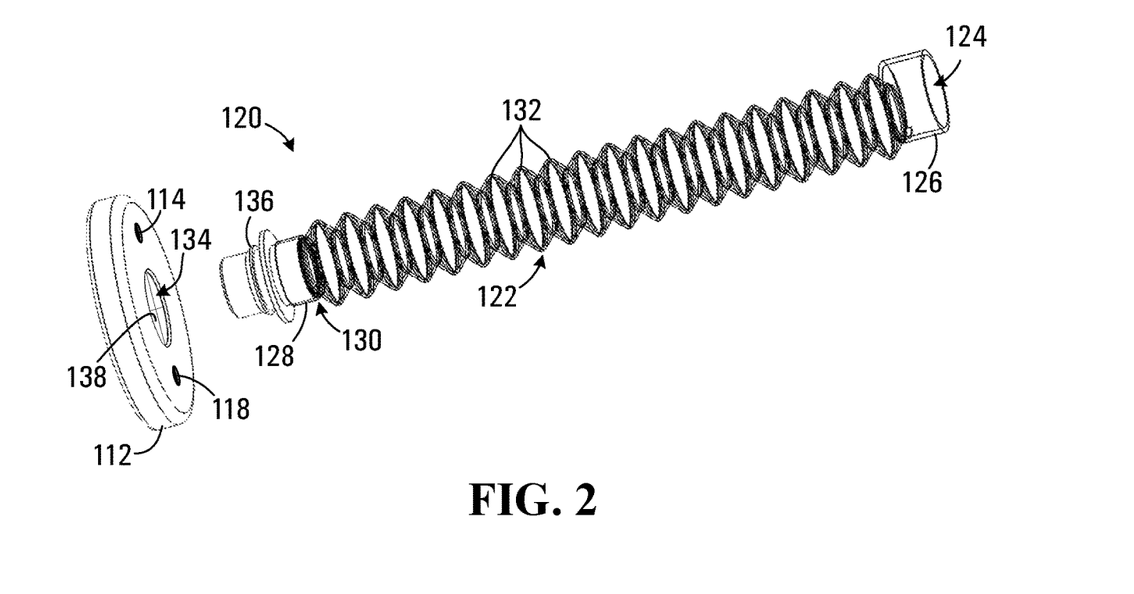
FIG. 2 is a perspective view of an access port and an apparatus according to a first embodiment of the invention for providing access for a surgical procedure within a body cavity of the patient shown in FIG. 1.

Referring to FIG. 2, an apparatus for providing surgical access to a body cavity of the patient 100 according to a first embodiment of the invention is shown generally at 120. The apparatus 120 includes a collapsible volume 122 and an opening 124 in communication with the collapsible volume. In this embodiment the opening 124 is provided by a collar 126 for receiving and sealing to a surgical apparatus such as a portion of a robotic surgical system (not shown in FIG. 2). The apparatus 120 further includes an access coupler 128 disposed at a distal end 130 of the collapsible volume 122. In this embodiment the collapsible volume 122 is provided by a bellowed conduit extending between the collar 126 and the access coupler 128. The bellowed conduit encloses the collapsible volume 122 and includes a plurality of convoluted sections 132 formed end to end that have sufficient compliance to permit the conduit to be flexibly extended or compressed.

In the embodiment shown, the access port 112 includes an opening 134 and the access coupler 128 is configured to sealingly couple to the opening. In this embodiment the access coupler 128 includes a barbed end 136 that engages corresponding features in the opening 134 for retaining and/or sealing the access coupler to the access port 112.

In other embodiments, the access coupler 128 may be configured for coupling to other access ports having different openings, sealing, and retaining configurations. For example the access coupler 128 may include a bayonet-type twist lock connection.

Figure 3:
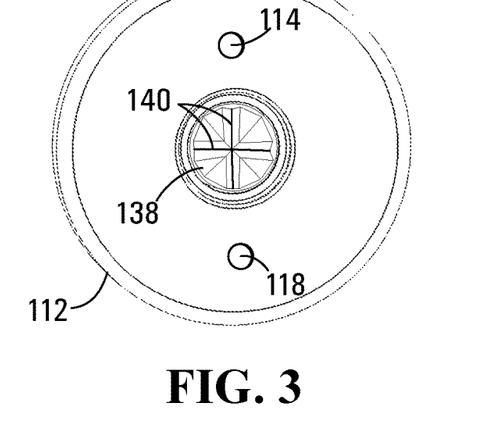
FIG. 3 is a front perspective view of the access port shown in FIG. 2.

In the embodiment shown the access port 112 includes an access valve 138 disposed in the opening 134. The access valve 138 provides a penetrable seal for sealing the opening 134 and thus the body cavity, prior to the access coupler 128 being received in the opening 134. The access port 112 and access valve 138 are shown in front perspective view in FIG. 3. Referring to FIG. 3, in one embodiment the access valve 138 is implemented using a duck-bill seal having displaceable cross-slits 140 that initially seal the opening 134 and are displaced by the access coupler 128 when received in the opening. In other embodiments the access valve 138 may be implemented using other types of sealing elements, such as a displaceable gel seal.

The access valve 138 facilitates installation of the access port 112 in the incision in the abdominal wall 105 while closing off incision to maintain sterile conditions within the body cavity of the patient 100. The access coupler 128 of the apparatus 120 may thus be coupled to the access port 112 after the access port 112 is installed. The opening 134 of the access port 112 remains closed by the access valve 138 until the access coupler 128 is coupled to the opening. The distal end 130 of the access coupler 128 displaces the access valve 138 placing the collapsible volume 122 in fluid communication with the body cavity through the access port 112. The body cavity may thus be insufflated before the apparatus 120 is coupled to the access port 112.

In other embodiments the access coupler 128 may be coupled to the access port 112 prior to the access port being inserted in the incision in the abdominal wall 105 and the access valve 138 may be omitted from the access port 112. In this case the apparatus 120 may include a seal that initially closes off the collapsible volume 122 to prevent escape of the insufflation gas through the opening 124 when connected to the access port 112. In one embodiment, the seal may be disposed in the opening 124 of the apparatus 120 and may include a valve such as the access valve 138 shown in FIG. 3. In another alternative embodiment, the collapsible volume 122 of the apparatus 120 may be sealed by a surgical apparatus that is received in the opening 124 prior to coupling the access coupler 128 to the access port 112. The access port 112, apparatus 120, and the surgical apparatus may thus be sealingly coupled together before insertion of the access port into the abdominal wall 105 of the patient 100.

Figure 4:
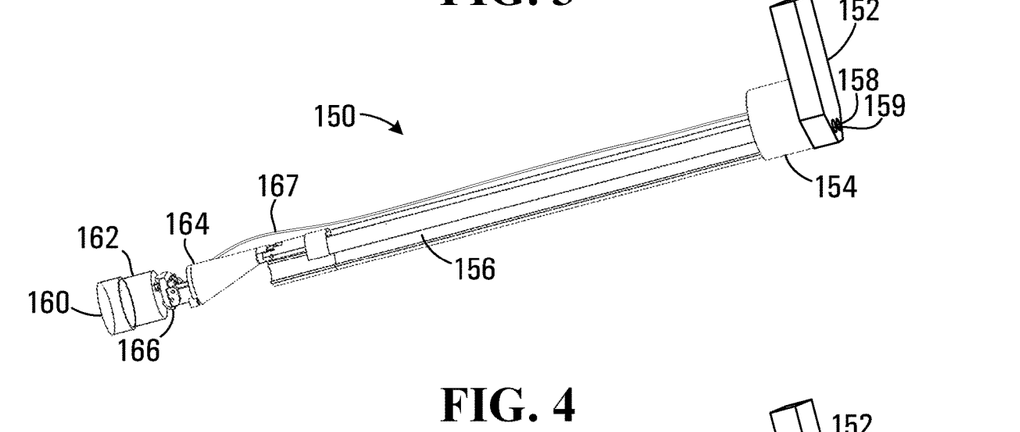
FIG. 4 is a perspective view of one embodiment of a surgical apparatus used during the surgical procedure.

Referring to FIG. 4 an example of a surgical apparatus is shown at 150. In the embodiment shown the surgical apparatus 150 is a portion of a robotic surgical system that is sized for insertion through the opening 134 in the access port 112. The surgical apparatus 150 includes an actuator interface 152, a bulkhead 154, and an elongate shaft 156 extending from the bulkhead. In this embodiment the surgical apparatus 150 has two bores 158 and 159 that run internally through the shaft 156 and are operable to receive a surgical instrument (not shown in FIG. 4). Each bores 158 and 159 may also include a closure such as a displaceable valve (not shown) for preventing escape of insufflation gas through the bores when not in use.

In the embodiment shown the surgical apparatus 150 also includes a camera 162 located at a distal end 160 of the shaft 156. The camera 162 is mounted on linkages 164 and 166, which are initially disposed to cause the camera to be axially aligned with the shaft 156. The actuator interface 152 includes actuators (not shown) for actuating the linkages 164 and 166 to deploy the camera 162 after insertion through the opening 134 in the access port 112. The camera 162 would also generally include an illumination source (not shown) for illuminating the body cavity. In the embodiment shown the surgical apparatus 150 includes a wash tube 167. During a surgical procedure, the wash tube 167 would be connected to a wash fluid supply operable to deliver wash fluid for cleaning lenses associated with the camera 162 and/or illumination source. In this embodiment, the wash tube 167 extends external to the shaft 156 between the bulkhead 154 and the camera 162. In other embodiments the wash tube 167 may be accommodated within a bore of the shaft 156. The wash fluid supply would generally include a reservoir of wash fluid and a pump (not shown) for delivering the wash fluid through the wash tube 167.

While the embodiments herein are described with reference to the specific example of the surgical apparatus 150 shown in FIG. 4, other robotic and/or laparoscopic surgical instruments may be used in conjunction with the apparatus 120.

Figure 5:
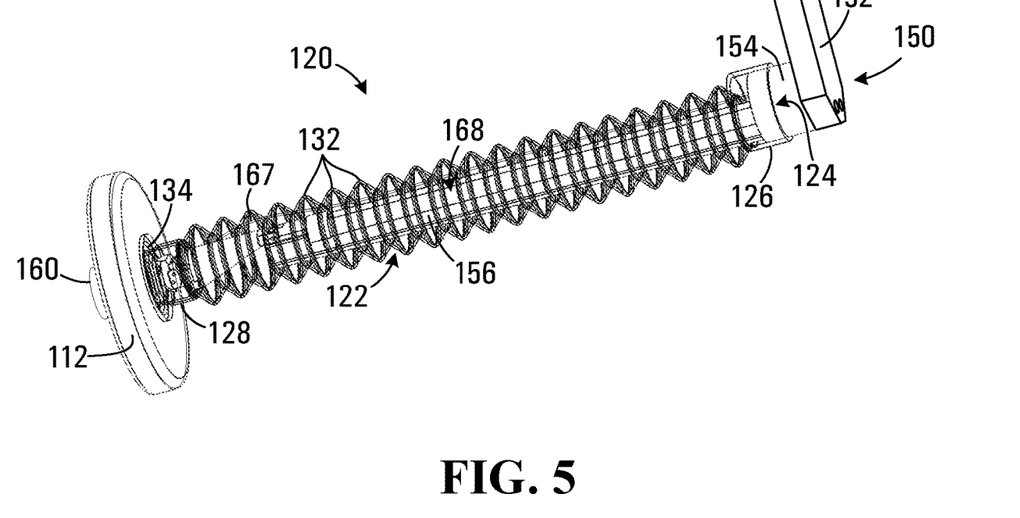
FIG. 5 is a perspective view of the apparatus shown in FIG. 2 receiving the surgical apparatus shown in FIG. 4.

Referring to FIG. 5, the surgical apparatus 150 is shown being received in the opening 124 of the apparatus 120. The shaft 156 of the surgical apparatus 150 has been received through the opening 124 such that at least a portion 168 extends into the collapsible volume 122. In FIG. 5, the access coupler 128 has already been coupled to the opening 134 of the access port 112. Alternatively, when the access port includes an access valve as described above, the surgical apparatus 150 may be inserted into the opening 124 of the apparatus 120 prior to coupling the access coupler 128 to the access port 112.

In the embodiment shown, the bulkhead 154 has a generally cylindrical cross section having a diameter selected to correspond to a diameter of the collar 126. The collar 126 provides a sufficient seal at the bulkhead 154 for maintaining insufflation pressure within the body cavity when the apparatus 120 is connected to the access port 112. In general, sealing of the body cavity at the access port 112 and bulkhead 154 should be sufficient to prevent any significant leakage of insufflation gas. Maintaining low leakage conserves insufflation gas by minimizing a required inflow of gas for purposes of maintaining the insufflation pressure and also reduces drying out of the body cavity. In one embodiment the collar 126 may be fabricated from a compliant material such as a thermoplastic that is able to stretch over the bulkhead 154 to provide an adequate seal and to maintain engagement with the surgical apparatus 150 during the surgical procedure. In other embodiments, the collar 126 may be configured to engage the bulkhead 154 using an interlocking coupler such as a bayonet or snap-on connector and an o-ring may be provided between the collar and the bulkhead for maintaining an adequate seal.

When the access coupler 128 is coupled to the opening 134 of the access port 112, fluid communication is provided between the collapsible volume 122 and the body cavity, thus extending the insufflated volume of the body cavity to include the collapsible volume. The collapsible volume 122 is thus subjected to the insufflation pressure in the body cavity when coupled to the access port 112. The collapsible volume 122 may be sized such that the portion 168 of the surgical apparatus 150 that extends into the collapsible volume does not initially protrude through the distal end 130 of the access coupler 128, such that the body cavity may be fully insufflated before the surgical apparatus is received within the body cavity. When the access port 112 includes an access valve 138, the collapsible volume 122 would be sized such that the access coupler 128 causes the access valve to open prior to any portion of the surgical apparatus 150 being received through the opening. The camera 162 at the distal end 160 therefore need not push through the access valve 138, which may risk occlusion of camera lenses. Additionally no sharp objects such as laparoscopic instruments are required to push through the access valve 138, which may compromise the seal provided by the access valve.

In other embodiments, the access coupler 128 and access port 112 may be configured for coupling using alternative sealing and retaining configurations, such as a bayonet-type twist lock. Additionally the retaining configuration may be further configured to provide a secure interlocking feature (not shown) preventing the access coupler from de-coupled until the interlock is released.

In FIG. 5, the collapsible volume 122 is shown in a partially extended state, in which the plurality of convoluted sections 132 are only slightly compressed or slightly extended. In this state the collar 126 of the apparatus 120 and the bulkhead 154 of the surgical apparatus 150 may be advanced toward the access coupler 128 while compressing the plurality of convoluted sections 132, causing the distal end 160 of the surgical apparatus 150 to move toward the access port 112 to facilitate insertion of the surgical apparatus into the body cavity. The compression of the plurality of convoluted sections 132 requires only minimal force and the collapsible volume 122 is sized to permit free movement of the shaft 156 of the surgical apparatus 150 toward the body cavity while permitting some lateral movement within lateral confines of the collapsible volume. The lateral movement facilitates alignment of the surgical apparatus 150 for insertion through the access coupler 128 and through the opening 134 in the access port 112.

In the embodiment shown in FIG. 5 the collapsible volume 122 is at least partially transparent and permits the surgical apparatus 150 to be viewed while being inserted through the access coupler 128 and the opening 134 in the access port 112 and into the body cavity (not shown). Transparency of the collapsible volume 122 thus acts as an aid to the surgeon for aligning the distal end 160 of the surgical apparatus 150 during insertion through the access coupler 128 and opening 134 into the body cavity.

Figure 6:
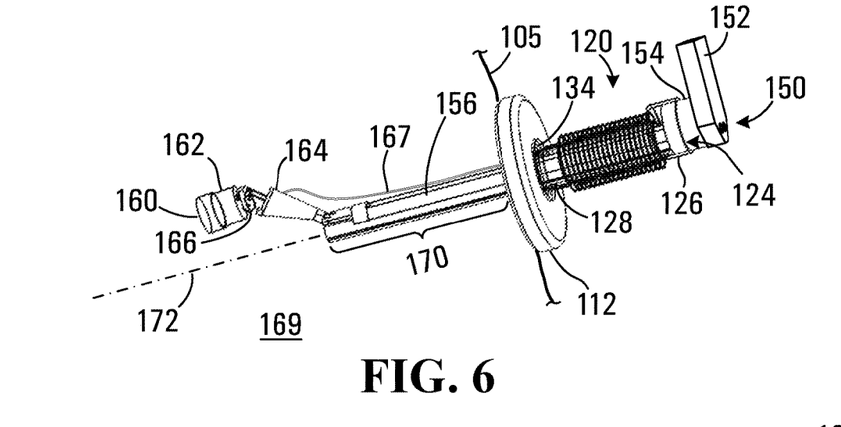
FIG. 6 is a perspective view of the apparatus shown in FIG. 5 in a collapsed state.

Referring to FIG. 6, the access port 112 is shown installed in the abdominal wall 105 of the patient 100 and the body cavity 169 (represented to the left of the abdominal wall 105 in FIG. 5). The plurality of convoluted sections 132 have been compressed causing the surgical apparatus 150 to be advanced through the access port 112 in a direction aligned with an axis 172 of the shaft 156. The distal end 160 of the surgical apparatus 150 has thus entered the body cavity 169 and a portion 170 of the shaft 156 also extends into the body cavity. Axial translation of the surgical apparatus 150 in either direction along the axis 172 may be provided manually by an attendant or the surgeon or may be provided by a drive actuator (not shown) attached to the actuator interface 152 or bulkhead 154.

The opening 134 of the access port 112 and the access coupler 128 may be sized to permit free axial movement of the shaft 156 within the access port 112. The movements can occur within the bounds provided by the collapsible volume 122, the access coupler 128, and the opening 134. The access valve 138 is displaced by the access coupler 128 when initially connected and does not provide any further constraint to movement of the shaft 156. The apparatus 120 thus extends the insufflation volume into the collapsible volume 122 and also removes the need for a sliding seal at the access port 112 that would be commonly required for robotic or laparoscopic surgery.

The collapsible volume 122 and access coupler 128 may additionally be sized to accommodate additional lines or tubes for operating the surgical apparatus 150. For example, while the wash tube for the camera 162 may be accommodated in a bore within the shaft 156, the available space within the bore may be limited due to constraints on the diameter of the shaft and space within the bore required for other purposes. The diameter of the collapsible volume 122 of the apparatus 120 may thus be selected to facilitate running the wash tube 167 external to the shaft 156. Since the collapsible volume 122 is sealed from the environment, no additional sliding seal would be required for the wash line 167, which would extend through the collapsible volume 122 and the opening 134 within the insufflated volume. Other lines may also be run through the collapsible volume 122. For example, signal or power lines associated with camera operation may also be run external to the shaft 156 within the collapsible volume 122.

When the surgical apparatus 150 has accessed the body cavity 169 as shown in FIG. 6, the linkages 164 and 166 may be actuated to cause the camera 162 to be deployed by moving laterally away from the axis 172. Further actuation of the linkages 164 and 166 may be employed to articulate the camera 162 as necessary for viewing and/or illuminating the surgical site within the body cavity. The surgical apparatus 150 may also be further moved axially along the longitudinal axis 172 in either direction to initially dispose the surgical apparatus 150 proximate the surgical site in the body cavity 169 and to place the camera 162 in a suitable location for viewing and illuminating the surgical site. The plurality of convoluted sections 132 of the collapsible volume 122 facilitate such axial movements by compressing or retracting as necessary depending on the size of the body cavity 169 and the location of the surgical site within the body cavity. In general the length of the collapsible volume 122 may be selected to provide sufficient axial translation range of the surgical apparatus 150 for both larger and smaller body cavities 169.

Figure 7:
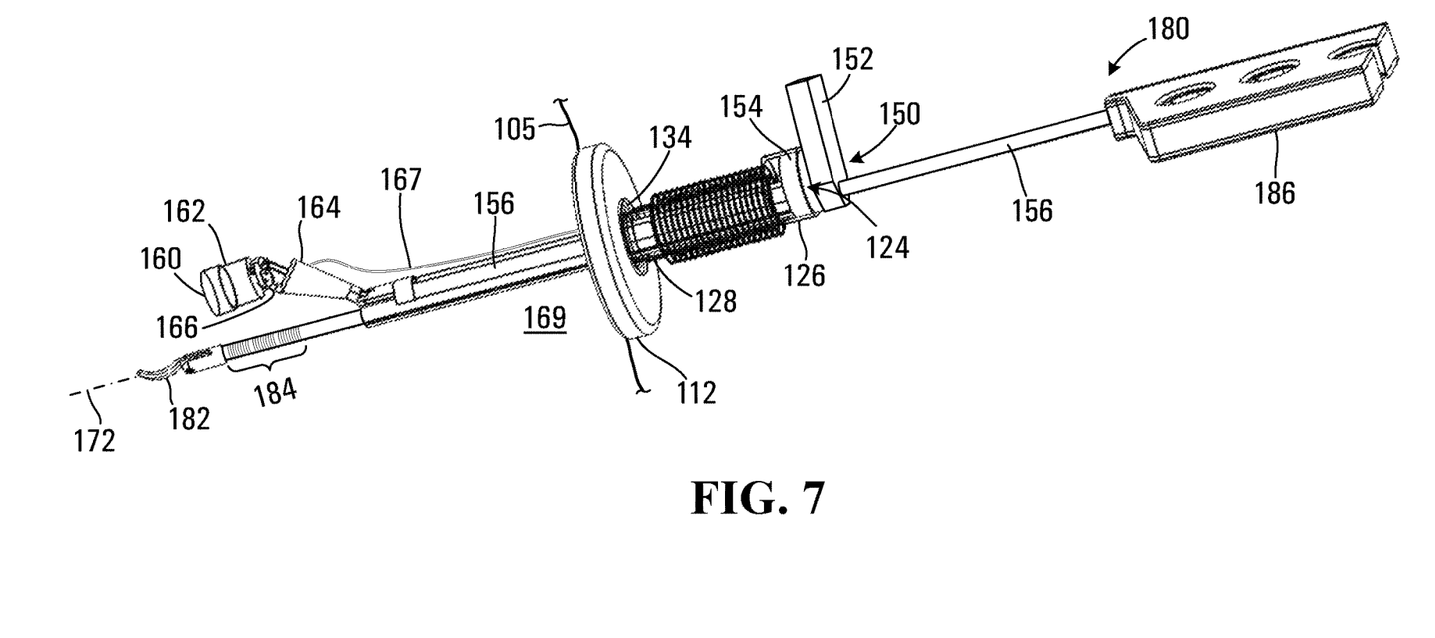
FIG. 7 is a perspective view of the apparatus shown in FIG. 6 receiving a surgical instrument.

Referring to FIG. 7, deployment of the camera 162 provides clearance for a surgical instrument 180 to be introduced into one of the bores 158 and 159 of the surgical apparatus 150 and advanced through the shaft 156 to access the body cavity 169. In the embodiment shown, the surgical instrument 180 has a tool 182 disposed at its distal end, which protrudes from the end of the shaft 156 and is disposed to perform surgical operations within the body cavity 169. The tool 182 may be any of a variety of tools such as are generally used in laparoscopic surgery such as surgical scissors, forceps, or an electrocauterization tool. In the embodiment shown an additional surgical instrument (not shown) may be inserted through a remaining one of the bores 158 and 159. While the surgical apparatus 150 described herein is configured to receive the surgical instrument 180 through the bores 158 and 159, in other embodiments the surgical instrument may be an integral part of the surgical apparatus 150 and the apparatus 120 may be configured to directly receive the surgical instrument.

Once inserted, the surgical instrument 180, tool 182, and the camera 162 may be remotely controlled by a surgeon. In the embodiment shown in FIG. 7, a portion 184 of the surgical instrument 180 is configured as an articulated tool positioner as described in detail in commonly owned patent applications PCT/CA2013/001076 entitled "ARTICULATED TOOL POSITIONER AND SYSTEM EMPLOYING SAME" and PCT/CA2015/000098 entitled "ACTUATOR AND DRIVE FOR MANIPULATING A TOOL" filed on Feb. 28, 2015. The articulated tool positioner permits dexterous movement of the portion 184 and thus the tool 182 in response to actuation forces received at an instrument interface 186. In addition to the dexterous movement provided by the portion 184 of the surgical instrument 180, further axial movements of the surgical apparatus 150 and the surgical instrument 180 within the bore 158 or 159 are provided by an instrument drive (not shown), which may be coupled to the instrument interface 186. The instrument drive is operable to cause movement of the surgical instrument 180 in a direction aligned with the longitudinal axis 172 of the shaft 156 for advancing or retracting the surgical instrument 180 within the bore 158 or 159. Additionally, should the surgical instrument 180 need to be repositioned within the body cavity 169, the surgical apparatus 150 may be axially moved to a new location, either extending or compressing the plurality of convoluted sections 132 of the collapsible volume 122. The combination of independent axial movements of the surgical apparatus 150 and the surgical instrument 180 may be employed during the surgical procedure to reposition the camera 162 and/or tool 182 as necessary for performing surgical operations within the body cavity 169.

In the embodiment shown in FIGS. 4-7 the bulkhead 154 of the surgical apparatus 150 and the collar 126 both have generally circular cross sections. In other embodiments, the collar 126 may be configured to accept a surgical apparatus 150 having a non-circular cross section or to accept other lines for operating the surgical apparatus. In the embodiment shown in FIG. 2, the opening 134 of the access port 112 is shown as being centered within the access port. However, in other embodiments the opening 134 may be located off center and additional ports for auxiliary instruments and/or lines may also be provided in the access port 112. In one embodiment the apparatus 120 may be fabricated using a relatively inexpensive plastic and/or elastic materials. The apparatus 120 may be packed in sterile packaging for a single use and discarded once the surgery is completed. In other embodiments the apparatus 120 may be fabricated from more durable material and may be used for a predetermined number of uses and sterilized after each use.

Figure 8:
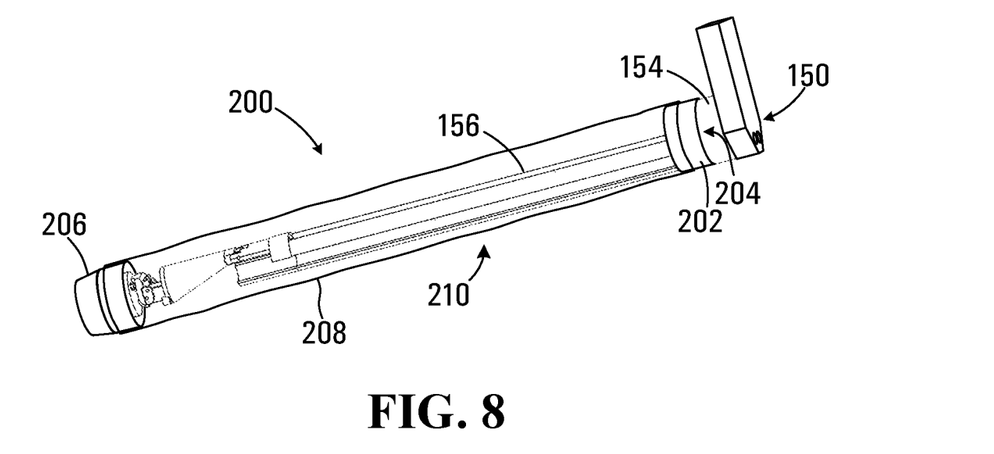
FIG. 8 is a perspective view of an apparatus according to another embodiment of the invention for providing access for a surgical procedure within a body cavity of the patient shown in FIG. 1.

Referring to FIG. 8, an apparatus for providing access for a surgical procedure within a body cavity of a living animal according to another embodiment of the invention is shown generally at 200. The apparatus 200 includes a collar 202 having an opening 204 for receiving the surgical apparatus 150. The apparatus 200 also includes an access coupler 206. In this embodiment a flexible sleeve 208 extends between the collar 202 and the access coupler 206 and provides the collapsible volume 210. In one embodiment the flexible sleeve 208 may be fabricated using a transparent polythene material. The shaft 156 of the surgical apparatus 150 is received in the opening 204 of the bulkhead 154 and seals to the collar 202 as generally described above.

Figure 9:
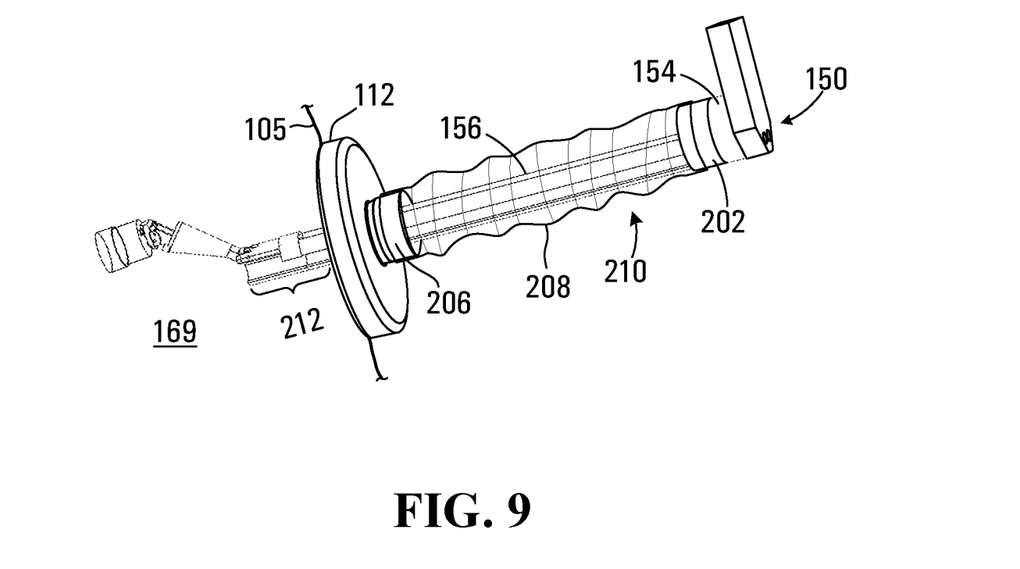
FIG. 9 is a perspective view of the apparatus shown in FIG. 8 in a collapsed state.

Referring to FIG. 9, when the access coupler 206 is coupled to the access port 112, the collar 202 and bulkhead 154 may be advanced toward the access coupler 206 and the access port 112 such that a portion 212 of the surgical apparatus 150 extends through the access coupler and into the body cavity 169. The flexible sleeve 208 is able to fold and/or crumple to facilitate movement while inserting the surgical apparatus 150 through the access coupler 206 into the body cavity 169. Similarly when retracting the surgical apparatus 150 the flexible sleeve 208 unfolds and/or stretches while maintaining the sealed body cavity 169. When coupled to the access port 112, the collapsible volume 210 is subjected to the insufflation pressure from the body cavity, which has the tendency keep the flexible sleeve 208 inflated, thus facilitating free passage for the surgical apparatus 150 within the volume. The apparatus 200 may be packed in sterile packaging for a single use and discarded after the surgery.

In other embodiments, the collapsible volume 122 or 210 may be provided by an inflexible sleeve. For example, the sleeve may include a plurality of telescoping segments having sliding seals between the segments.

The above embodiments provide convenient deployment and insertion of a surgical apparatus for a surgical procedure. The need for a sliding seal is eliminated in favor of more simple static seals or valves provided between the collar (126, 204) and the device 150 and also at the opening 134 of the access port 112. In this case there is no need to overcome sliding friction associated with seals used in many robotic surgery access ports and the action of coupling the access coupler (128, 206) to the access port 112 may thus result in reduced forces applied to the access port 112 and the abdominal wall 105. Furthermore, subsequent movements of the surgical apparatus 150 back and forth within the body cavity would also only exert minimal force on the access port 112 since free access is provided through the opening 134. Furthermore, for a surgical apparatus having a non circular shaft cross section there is no further constraint at the access port due to complex sealing requirements since the access valve 138 is displaced to open by connecting the access coupler (128, 206) and the access coupler may be sized to accommodate the instrument cross section. Additional lines such as a wash tube for delivering wash fluid for lens cleaning may also be run through the collapsible volume (122, 210) and access coupler (128, 206) without additional complexity in coupling through the access port 112. Again, the access coupler (128, 206) and access port 112 need only be sized to accommodate the additional lines.

Figure 10:
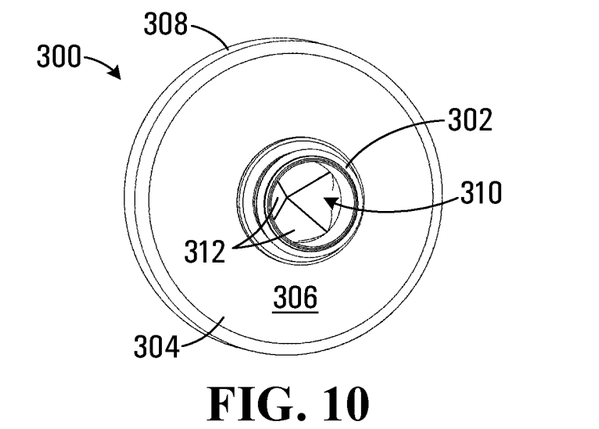
FIG. 10 is a perspective view of an alternative access port embodiment.

Referring to FIG. 10, an alternative embodiment of an access port is shown at 300. In this embodiment the access port 300 is provided by a valve conduit 302 inserted through a gel seal 304. The gel seal 304 may be the GelPOINT access platform manufactured by Applied Medical of California, USA, which includes a displaceable gel portion 306 surrounded by a substantially rigid rim 308. The rim 308 may be configured to attach to the access device 104 shown in FIG. 1. The valve conduit 302 includes an access valve 310 implemented using a duck-bill seal having displaceable cross-slits 312.

Figure 11:
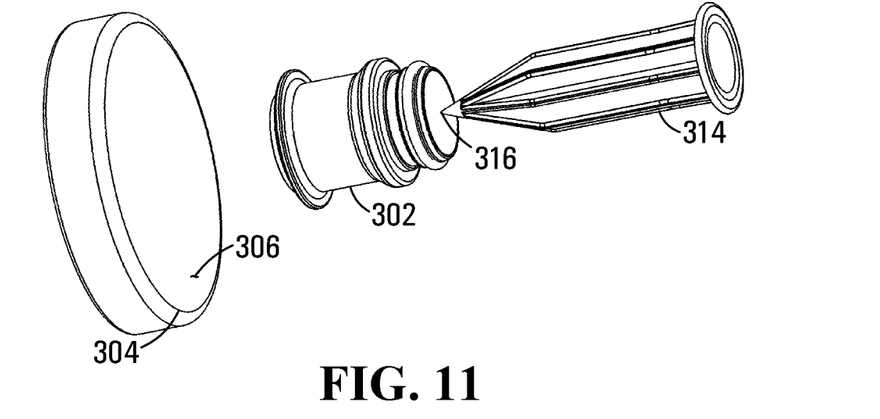
FIGS. 11-13 are a series of views depicting insertion of a valve conduit into a gel seal for configuring the access port shown in FIG. 10.
Figure 12:
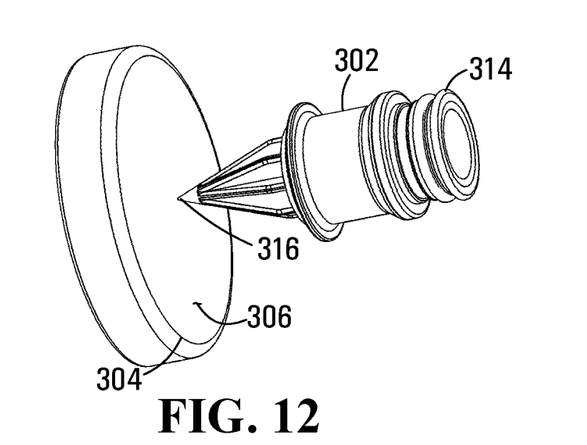
Figure 13:
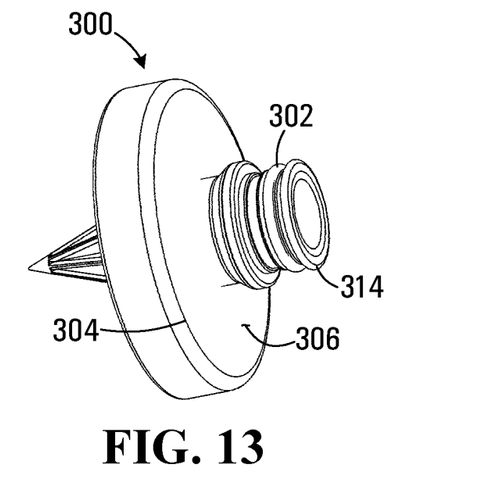

In one embodiment the valve conduit 302 and gel seal 304 may be supplied in separate sterile packaging (not shown) and the valve conduit may be inserted through the gel seal 304 prior to use. Referring to FIG. 11, a sterile obturator 314 having a sharp tip 316 may be provided together with the valve conduit 302 for piercing the gel portion 306 of the gel seal 304. Referring to FIG. 12, the obturator 314 is inserted through the valve conduit 302 and the sharp tip 316 is pressed through the gel portion 306 of the gel seal 304. The inserted valve conduit 302 is shown in FIG. 13, and following insertion of the access conduit, the sterile obturator 314 may be removed and discarded. The access port 300 may then be coupled to the access device 104 generally as shown in FIG. 1. In this embodiment the gel seal 304 is sized to provide a free area of the gel portion 306 surrounding the valve conduit 302 to permit additional access through the abdominal wall 105 of the patient 100 for additional instruments or the surgeon's fingers etc.

Figure 14:
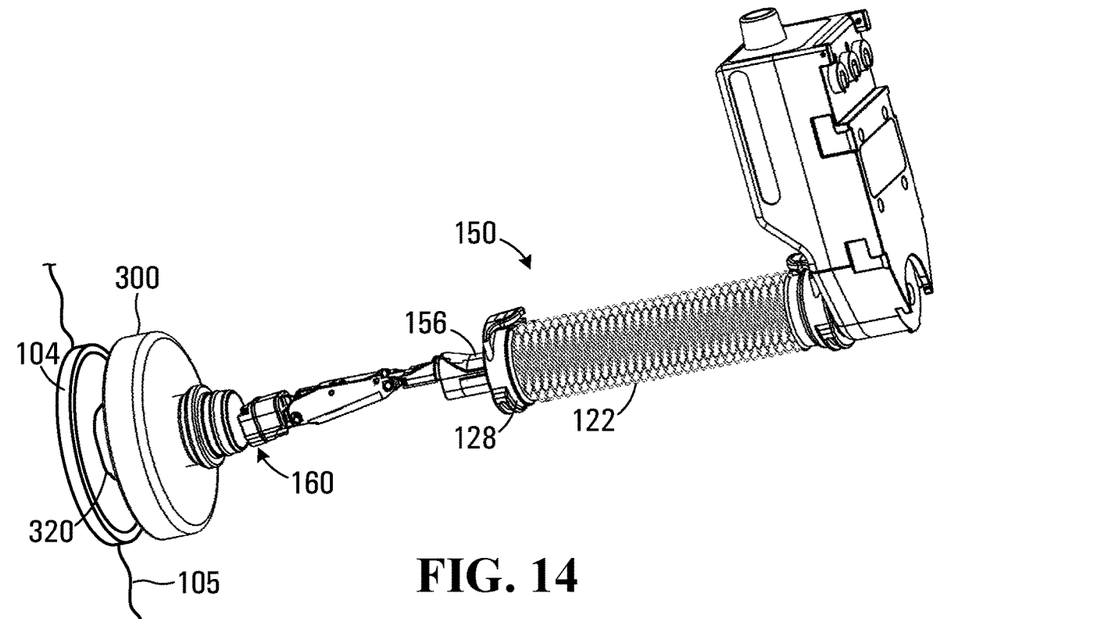
FIG. 14 is a perspective view of the surgical apparatus of FIG. 4 being received in the access port shown in FIG. 10.
Figure 15:
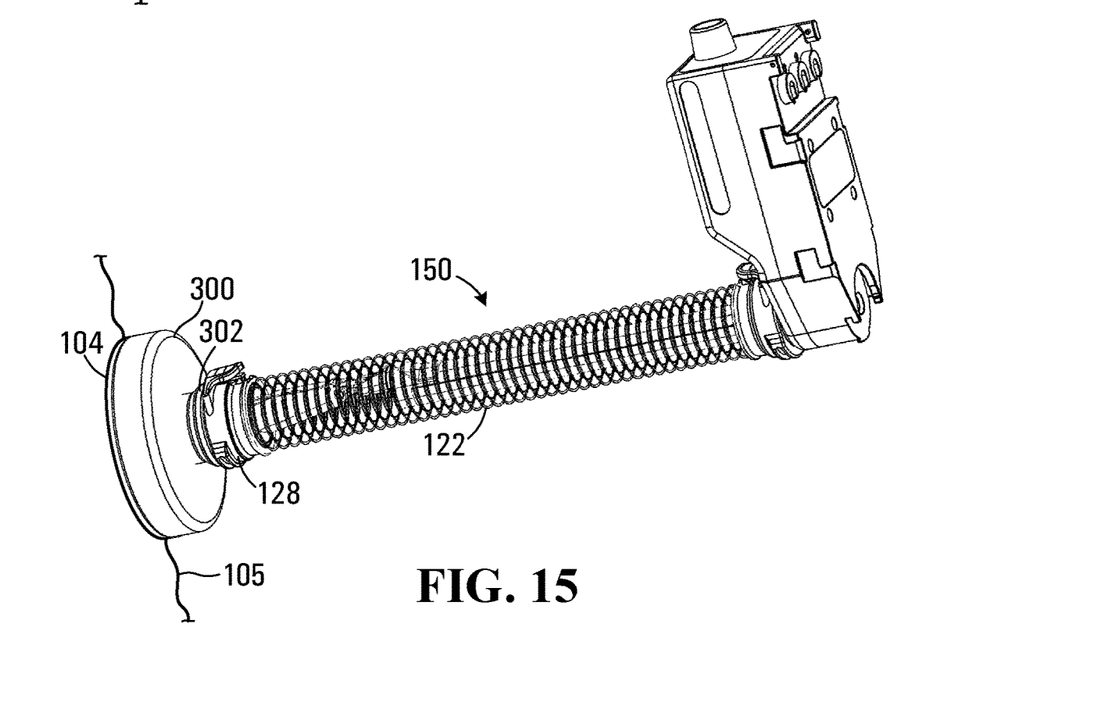
FIG. 15 is a perspective view of the surgical apparatus of FIG. 4 coupled to the access port shown in FIG. 10.

In FIG. 14 the access port 300 is shown being attached to the access device 104 that retracts to provide an opening 320 in the abdominal wall 105 of the patient. In one embodiment the surgical apparatus 150 (shown in FIG. 4) is inserted through the valve conduit 302 of the access port 300. The displaceable cross-slits 312 of the access valve 310 permit the distal end 160 of the surgical apparatus 150 to access the patient's body cavity through the access port 300. In this embodiment the collapsible volume 122 is initially maintained in a collapsed state with the access coupler 128 partway along the shaft 156. Referring to FIG. 15 the access coupler 128 is then 30 sealingly coupled to the valve conduit 302 and the distal end 160 of the surgical apparatus 150 is able to enter the body cavity through the access valve 310 (shown in FIG. 10). When the access valve 310 is breeched by the distal end 160 of the surgical apparatus 150, the collapsible volume 122 is placed in fluid communication with the body cavity.

While specific embodiments of the invention have been described and illustrated, such embodiments should be considered illustrative of the invention only and not as limiting the invention as construed in accordance with the accompanying claims.

What is claimed is:

1. A method for providing surgical access to a body cavity of a patient through an access port, the method comprising:
engaging an access port to an entry point into a body cavity of a patient;
receiving a surgical apparatus through an opening in a collapsible volume;
after engaging the access port and after receiving the surgical apparatus through the opening in the collapsible volume, coupling an access coupler of the collapsible volume to an opening in the access port such that the collapsible volume is placed in fluid communication with the body cavity; and
after coupling the access coupler to the opening in the access port, causing the collapsible volume to collapse such that at least a portion of the surgical apparatus is configured to be inserted through the access coupler and into the body cavity.

2. The method of claim 1 further comprising:
receiving fluid through an inlet of the access port and into the body cavity to insufflate at least a portion of the body cavity; and
subjecting the collapsible volume to insufflation pressure in the body cavity.

3. The method of claim 2 further comprising opening an access valve of the access port to initiate fluid communication between the body cavity and the collapsible volume.

4. The method of claim 3, wherein opening the access valve comprises displacing a sealing element of the access valve, and wherein the sealing element is configured to be displaced when the access coupler is coupled to the opening in the access port.

5. The method of claim 1 further comprising expelling fluid out of the body cavity through an outlet of the access port.

6. The method of claim 1, wherein coupling the access coupler to the opening in the access port comprises engaging the access coupler to the access port such that the access coupler is configured to be at least partially retained within the opening in the access port.

7. The method of claim 1, wherein the collapsible volume comprises a flexible sleeve configured to receive the surgical apparatus.

8. The method of claim 7, wherein the flexible sleeve comprises a transparent portion configured to permit at least the portion of the surgical apparatus to be viewed when the portion is inserted through the access coupler and through the opening in the access port.

9. The method of claim 1, wherein the collapsible volume comprises a bellowed conduit.

10. The method of claim 1, wherein receiving the surgical apparatus through the opening of the collapsible volume comprises receiving the surgical apparatus through a collar of the collapsible volume.

11. The method of claim 10, wherein the collar comprises a non-circular cross section configured to correspond to a non-circular cross section of the surgical apparatus.

12. The method of claim 1, wherein the surgical apparatus comprises at least one of:
a camera configured to view the body cavity;
an illumination source configured to illuminate the body cavity;
a wash tube configured to deliver a wash fluid for cleaning a lens of the surgical apparatus; or
a bore configured to receive a laparoscopic surgery instrument.

13. The method of claim 1, wherein the collapsible volume is configured to permit lateral movement of the surgical apparatus with respect to the access coupler to facilitate alignment of the surgical apparatus for insertion through the access port.

14. The method of claim 1 further comprising receiving at least one line through the collapsible volume, through the access port, and into the body cavity, wherein the at least one line comprises one or more of:
an electrical signal line;
an optical signal line;
a power line; or
a wash tube configured to clean a lens of a camera disposed on a distal end of the surgical apparatus.

15. A method for providing surgical access to a body cavity of a patient through an access port, the method comprising:
receiving a surgical apparatus through an opening in a collapsible volume;
coupling an access coupler of the collapsible volume to an opening in the access port such that the collapsible volume is placed in fluid communication with the body cavity; and
causing the collapsible volume to collapse such that at least a portion of the surgical apparatus is configured to be inserted through the access coupler and into the body cavity,
wherein the access port comprises:
an access valve configured to close the opening in the access port when the access coupler is not coupled to the opening;
an inlet being separate from the opening, the inlet being configured to receive fluid to insufflate at least a portion of the body cavity; and
an outlet being separate from the opening, the outlet being configured to receive fluid to expel fluid out of the body cavity.

16. The method of claim 15 further comprising:
receiving fluid through the inlet of the access port and into the body cavity to insufflate at least the portion of the body cavity; and
subjecting the collapsible volume to insufflation pressure in the body cavity.

17. The method of claim 15 further comprising opening the access valve of the access port to initiate fluid communication between the body cavity and the collapsible volume, wherein opening the access valve comprises displacing a sealing element of the access valve, and wherein the sealing element is configured to be displaced when the access coupler is coupled to the opening in the access port.

18. The method of claim 15 further comprising expelling fluid out of the body cavity through the outlet of the access port.

19. The method of claim 15, wherein the collapsible volume comprises a flexible sleeve configured to receive the surgical apparatus, and wherein the flexible sleeve comprises a transparent portion configured to permit at least the portion of the surgical apparatus to be viewed when the portion is inserted through the access coupler and through the opening in the access port.

20. The method of claim 15, wherein receiving the surgical apparatus through the opening of the collapsible volume comprises receiving the surgical apparatus through a collar of the collapsible volume, and wherein the collar comprises a non-circular cross section configured to correspond to a non-circular cross section of the surgical apparatus.

\* \* \* \* \*